United States Patent [19]

Audousset et al.

[11] Patent Number: 5,752,983
[45] Date of Patent: May 19, 1998

[54] COMPOSITION FOR OXIDATION DYEING OF KERATINOUS FIBRES COMPRISING AN OXIDATION BASE, A COUPLER, AND 4-HYDROXYINDOLE AS COUPLER AND DYEING PROCESS WITH THIS COMPOSITION

[75] Inventors: Marie-Pascale Audousset, Asnieres; Jean Cotteret, Verneuil sur Seine, both of France

[73] Assignee: L'Oreal, France

[21] Appl. No.: 589,390

[22] Filed: Jan. 22, 1996

[30] Foreign Application Priority Data

Jan. 20, 1995 [FR] France .................................. 95-00661

[51] Int. Cl.$^6$ .................................................. A61K 7/13
[52] U.S. Cl. ........................... 8/409; 8/408; 8/410; 8/411; 8/412
[58] Field of Search .......................... 8/406, 408, 409, 8/410, 411, 412, 416, 421, 423

[56] References Cited

U.S. PATENT DOCUMENTS

| | | | |
|---|---|---|---|
| 4,725,282 | 2/1988 | Hoch et al. | 8/408 |
| 4,797,130 | 1/1989 | Clausen et al. | 8/421 |
| 4,997,451 | 3/1991 | Clausen et al. | 8/421 |
| 5,021,066 | 6/1991 | Aeby et al. | 8/408 |
| 5,061,289 | 10/1991 | Clausen et al. | 8/406 |
| 5,225,965 | 7/1993 | Clausen et al. | 8/411 |
| 5,391,206 | 2/1995 | Cotteret | 8/408 |
| 5,409,503 | 4/1995 | Neunhoeffer et al. | 8/409 |
| 5,480,459 | 1/1996 | Mager et al. | 8/408 |
| 5,518,505 | 5/1996 | Cotteret | 8/423 |
| 5,534,267 | 7/1996 | Neunhoeffer et al. | 8/409 |
| 5,540,738 | 7/1996 | Chan et al. | 8/412 |
| 5,542,952 | 8/1996 | Genet et al. | 8/412 |
| 5,542,953 | 8/1996 | Balzer et al. | 8/408 |

FOREIGN PATENT DOCUMENTS

| | | |
|---|---|---|
| A-0428441 | 5/1991 | European Pat. Off. . |
| A-0465340 | 1/1992 | European Pat. Off. . |
| A-3031709 | 4/1982 | Germany . |
| A-3743769 | 7/1989 | Germany . |
| A-3942294 | 6/1991 | Germany . |

OTHER PUBLICATIONS

English language translation of DE 3,031,709, Wella, pp. 1–12, Apr. 1982.

*Primary Examiner*—Paul Lieberman
*Assistant Examiner*—Caroline L. Duscheck
*Attorney, Agent, or Firm*—Finnegan, Henderson, Farabow, Garrett & Dunner, L.L.P.

[57] ABSTRACT

The invention relates to a ready-for-use composition for the oxidation dyeing of keratinous fibres, in particular human keratinous fibres such as hair, including an oxidation dye precursor in combination with 4-hydroxyindole, a benzene-based coupler and an oxidizing agent in an alkaline medium, and to the dyeing process making use of this composition.

27 Claims, No Drawings

COMPOSITION FOR OXIDATION DYEING OF KERATINOUS FIBRES COMPRISING AN OXIDATION BASE, A COUPLER, AND 4-HYDROXYINDOLE AS COUPLER AND DYEING PROCESS WITH THIS COMPOSITION

The present invention relates to a ready-for-use composition for the oxidation dyeing of keratinous fibres, in particular of human keratinous fibres such as hair, including, in an alkaline medium, an oxidation dye precursor in combination with 4-hydroxyindole, a benzene-based coupler and an oxidizing agent, and to the dyeing process making use of this composition. It also relates to a dyeing kit for the preparation of such a ready-for-use composition.

It is known to dye keratinous fibres and in particular human hair with dye compositions containing oxidation dye precursors, in particular ortho- or para-phenylenediamines, ortho- or para-aminophenols, generally called oxidation bases. The oxidation dye precursors, or oxidation bases, are colourless or weakly coloured compounds which, combined with oxidizing products, can give rise to coloured and colouring compounds by a process of oxidative condensation.

It is also known that the shades obtained with these oxidation bases can be varied by combining them with colouring couplers or modifiers, the latter being chosen especially from aromatic meta-diamines, meta-aminophenols, meta-diphenols and some indole-based compounds like 4-hydroxyindole.

The variety of the molecules involved where oxidation bases and couplers are concerned makes it possible to obtain a rich palette of colours.

The so-called "permanent" colour obtained by virtue of these oxidation dyes must, furthermore, satisfy a number of requirements. Thus, it must be free of inconvenience from a toxicological viewpoint, it must make it possible to obtain shades of desired intensity and must have good resistance when faced with external agents (light, inclement weather, washing, permanent waving, perspiration, rubbing).

The dyes must also make it possible to cover white hair and, finally, be as nonselective as possible, that is to say make it possible to obtain colour differences which are as small as possible throughout the length of the same keratinous fibre, which may, in fact, be differently sensitized (i.e. damaged) between its tip and its root.

Compositions have already been proposed, especially in German Patent Application DE 3 031 709, for the oxidation dyeing at alkaline pH of keratinous fibres, containing an oxidation base, 4-hydroxyindole as a coupler and optionally additional conventional couplers such as resorcinol. Such compositions are not, however, entirely satisfactory, especially with regard to the selectivity of the colours obtained.

Furthermore, German Patent Application DE 3 743 769 describes a composition for the oxidation dyeing at alkaline pH of keratinous fibres, containing 2,3-dimethyl-para-phenylenediamine as oxidation base in combination with a coupler which may be especially 4-hydroxyindole. Such compositions are not, however, entirely satisfactory, especially with regard to the resistance of the colours obtained towards permanent deformations and to repeated washing.

The present invention aims to propose new compositions for the oxidation dyeing of keratinous fibres and in particular of human keratinous fibres such as hair, which exhibit very good tinctorial properties.

Thus, the applicants have, in fact, just discovered that it is possible to obtain new dyes which give rise to resistant, intense and relatively unselective colours, by using in combination:

- at least one oxidation base suitably selected and as defined below,
- 4-hydroxyindole as first coupler,
- at least one additional benzene-based coupler, suitably selected and as defined below,
- at least one oxidizing agent, the pH of the resulting dye composition being higher than or equal to 7.

This discovery is the basis of the present invention.

The first subject of the invention is therefore a ready-for-use composition for the oxidation dyeing of keratinous fibres and in particular of human keratinous fibres such as hair, characterized in that it includes, in a suitable medium for dyeing:

at least one oxidation base chosen from:

(i) the para-phenylenediamines of the following formula (I):

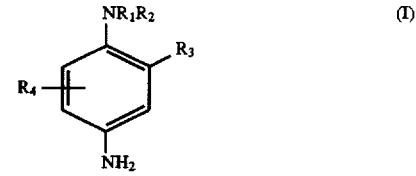

in which:

$R_1$ denotes a hydrogen atom or a $C_1$–$C_4$ alkyl, $C_1$–$C_4$ monohydroxyalkyl, $C_2$–$C_4$ polyhydroxyalkyl, $C_1$–$C_4$ alkoxyalkyl, phenyl or 4'-aminophenyl radical, $R_2$ denotes a hydrogen atom or a $C_1$–$C_4$ alkyl, $C_1$–$C_4$ monohydroxyalkyl or $C_2$–$C_4$ polyhydroxyalkyl radical, $R_3$ denotes a hydrogen atom, a halogen atom such as a chlorine atom or a $C_1$–$C_4$ alkyl, $C_1$–$C_4$ monohydroxyalkyl or $C_1$–$C_4$ hydroxyalkoxy radical, $R_4$ denotes a hydrogen atom or a $C_1$–$C_4$ alkyl radical, provided that, when $R_4$ is other than hydrogen, then $R_1$ and $R_2$ denote a hydrogen atom and $R_3$ is identical with $R_4$, and the addition salts of these compounds of formula (I) with an acid;

(ii) the para-aminophenols of the following formula (II):

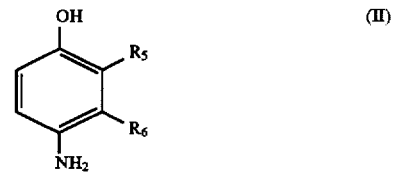

in which:

$R_5$ denotes a hydrogen atom or a $C_1$–$C_4$ alkyl, $C_1$–$C_4$ monohydroxyalkyl, $C_1$–$C_4$ alkoxyalkyl or $C_1$–$C_4$ aminoalkyl radical, $R_6$ denotes a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $C_1$–$C_4$ alkoxyalkyl radical, provided that at least one of the radicals $R_5$ and $R_6$ denotes a hydrogen atom.

and the addition salts of these compounds of formula (II) with an acid;

(iii) the heterocyclic bases chosen from pyridine derivatives such as, for example, those described in Patents GB 1 026 978 and GB 1 153 196, pyrimidine derivatives such as, for example, those described in German Patent DE 2 359 399 or Japanese Patents JP 88-169 571 and JP 91-333 495, pyrazole derivatives such as, for example, those described in Patents DE 3 843 892, DE 4 133 957 and DE 4 234 887 and the addition salts of these heterocyclic bases with an acid;

(iv) ortho-aminophenol;

4-hydroxyindole as first coupler;

at least one additional benzene-based coupler chosen from the compounds of the following formula (III) and their addition salts with an acid.

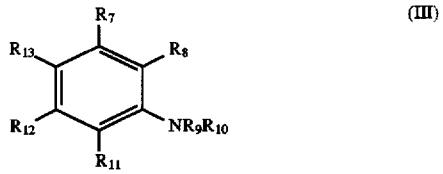

in which $R_7$ denotes an amino or hydroxyl radical, it being understood that:

when $R_7$ denotes an amino radical, then $R_8$ denotes a hydrogen atom or an alkyl radical, $R_9$ denotes a hydrogen atom, $R_{10}$ denotes a hydrogen atom or an alkyl, mono- or polyhydroxyalkyl radical, $R_{11}$ and $R_{12}$, which are identical or different, denote a hydrogen atom or an alkyl, mono- or polyhydroxyalkoxy radical, and $R_{13}$ denotes an alkoxy, aminoalkoxy or mono- or polyhydroxyalkoxy radical or a 2,4-diaminophenoxyalkoxy radical, provided that, if $R_{11}$ denotes a mono- or polyhydroxyalkoxy radical, then $R_{13}$ necessarily denotes a mono- or polyhydroxyalkoxy radical, when $R_7$ denotes a hydroxyl radical, then $R_8$ denotes a hydrogen atom, a halogen atom or an alkyl radical, $R_9$ denotes a hydrogen atom or an alkyl, mono- or polyhydroxyalkyl radical, $R_{10}$ denotes a hydrogen atom or an alkyl radical or forms with $R_9$ and the nitrogen atom a 5- or 6-cornered heterocyclic ring, $R_{11}$ denotes a hydrogen atom or an alkyl or alkoxy radical or a halogen atom, $R_{12}$ denotes a hydrogen atom and $R_{13}$ denotes a hydrogen atom or an alkyl, alkoxy, mono- or polyhydroxyalkyl, mono- or polyhydroxyalkoxy radical, provided that, if $R_8$ and $R_9$ simultaneously denote a hydrogen atom and $R_{13}$ a $C_1$–$C_4$ alkyl radical, then $R_{11}$ is necessarily other than a halogen atom or than a $C_1$–$C_4$ alkoxy radical, the above alkyl, alkoxy, monohydroxyalkyl and monohydroxyalkoxy radicals containing from 1 to 4 carbon atoms, the polyhydroxyalkyl and polyhydroxyalkoxy radicals containing from 2 to 4 carbon atoms and containing from 2 to 3 hydroxyl groups, the halogen atom denoting Chlorine, Fluorine or Bromine, at least one oxidizing agent, the pH of this ready-for-use dye composition being higher than or equal to 7.

The colours obtained with the dye compositions according to the invention are weakly selective and furthermore exhibit a good tinting power and excellent properties of resistance at the same time towards atmospheric agents such as light and inclement weather and to perspiration and various treatments to which hair may be subjected (repeated washing, permanent deformations).

Another subject of the invention is a process for oxidation dyeing of keratinous fibres making use of this dye composition.

The addition salts with an acid, which may be employed within the scope of the dye compositions of the invention, are chosen especially from hydrochlorides, hydrobromides, sulphates and tartrates.

Among the para-phenylenediamines of formula (I) above it is possible to mention more particularly para-phenylenediamine, para-tolylenediamine, 2-isopropyl-para-phenylenediamine, 2-β-hydroxyethyl-para-phenylenediamine, 2-β-hydroxyethoxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 1-β-methoxyethylamino-4-aminobenzene and their addition salts with an acid.

According to a particularly preferred embodiment of the invention the para-phenylenediamines of formula (I) above are chosen from para-phenylenediamine, para-tolylenediamine, 2-β-hydroxyethyl-para-phenylenediamine, 2,6-dimethyl-para-phenylenediamine, 2,3-dimethyl-para-phenylenediamine and N,N-bis(β-hydroxyethyl)-para-phenylenediamine and their addition salts with an acid.

Among the para-aminophenols of formula (II) above it is possible to mention more particularly para-aminophenol, 3-methyl-4-aminophenol, 3-fluoro-4-aminophenol, 3-hydroxymethyl-4-aminophenol, 2-methyl-4-aminophenol, 2-hydroxymethyl-4-aminophenol, 2-methoxymethyl-4-aminophenol, 2-aminomethyl-4-aminophenol, 2-(β-hydroxyethylaminomethyl)-4-aminophenol and their addition salts with an acid.

According to a particularly preferred embodiment of the invention the para-aminophenols of formula (II) above are chosen from para-aminophenol, 3-methyl-4-aminophenol, 3-fluoro-4-aminophenol and 3-hydroxymethyl-4-aminophenol and their addition salts with an acid.

Among the heterocyclic bases it is possible to mention more particularly 2,4,5,6-tetraaminopyrimidine, 2,5-diaminopyridine, 4,5-diamino-1-methylpyrazole, 3,4-diaminopyrazole, 4-hydroxy-2,5,6-triaminopyrimidine and their addition salts with an acid.

Among the additional benzene-based couplers of formula (III) above, it is possible to mention more particularly meta-aminophenol, 2-methyl-5-aminophenol, 5-N-(β-hydroxyethylamino)-2-methylphenol, 5-amino-2-methoxyphenol, 5-amino-2-(β-hydroxyethoxy)phenol, 5-N-(β-hydroxyethylamino)-4-methoxy-2-methylphenol, 5-amino-4-methoxy-2-methylphenol, 5-amino-4-chloro-2-methylphenol, 5-amino-2,4-dimethoxyphenol, 5-N-(γ-hydroxypropylamino)-2-methylphenol, 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 2,4-diamino-1-(β-hydroxyethoxy)benzene, 1-(β-aminoethoxy)-2,4-diaminobenzene, 2-amino-1-(β-hydroxyethoxy)-4-methylaminobenzene, 1,3-diamino-4,6-bis(β-hydroxyethoxy)benzene, 2,4-diamino-1-ethoxy-5-methylbenzene, 2,4-diamino-5-(β-hydroxyethoxy)-1-methylbenzene, 2,4-diamino-1-(β,γ-dihydroxypropoxy)benzene, 2-amino-4-N-(β-hydroxyethylamino)anisole and their addition salts with an acid.

According to a particularly preferred embodiment of the invention the additional couplers are chosen from the compounds of formula (III) in which $R_9$ and $R_{10}$ denote a hydrogen atom, such as, for example, meta-aminophenol, 2-methyl-5-aminophenol, 5-N-(β-hydroxyethylamino)-2-methylphenol, 2,4-diamino-1-(β-hydroxyethoxy)benzene, 1,3-bis(2,4-diaminophenoxy)propane, 1,3-diamino-4,6-bis(β-hydroxyethoxy)benzene and 2-amino-4-N-(β-hydroxyethylamino)anisole and their addition salts with an acid.

The combination of the oxidation bases in accordance with the invention, that is to say the para-phenylenediamine derivative(s) of formula (I) and/or the para-aminophenol(s) of formula (II) and/or the heterocyclic base(s) and/or the ortho-aminophenol preferably represents approximately from 0.0005 to 10% by weight of the total weight of the dye composition and, still more preferably approximately from 0.01 to 5% by weight.

4-Hydroxyindole preferably represents approximately from 0.0001 to 3.5% by weight of the total weight of the dye composition and, still more preferably, approximately from 0.005 to 1% by weight.

The additional benzene-based coupler(s) in accordance with the invention, that is to say the compound(s) of formula (III), preferably represent(s) approximately from 0.0001 to 5% by weight of the total weight of the dye composition and, still more preferably, approximately from 0.001 to 3% by weight.

The pH of the dye composition as defined above may vary between 7 and 12 and preferably between 8 and 11 and may be adjusted to the desired value by means of acidifying or alkalifying agents usually employed in the dyeing of keratinous fibres.

Among the acidifying agents there may be mentioned, by way of example, inorganic or organic acids such as hydrochloric acid, orthophosphoric acid, carboxylic acids such as tartaric acid, citric acid and lactic acid, and sulphonic acids.

Among the alkalifying agents there may be mentioned, by way of example, aqueous ammonia, alkali metal carbonates, alkanolamines such as mono-, di- and triethanolamines and their derivatives, sodium or potassium hydroxides and the compounds of formula (IV) which follows:

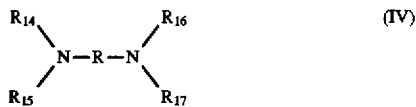

in which R is a propylene residue optionally substituted by a hydroxyl group or a $C_1$–$C_4$ alkyl radical; $R_{14}$, $R_{15}$, $R_{16}$ and $R_{17}$, which are identical or different, denote a hydrogen atom or a $C_1$–$C_4$ alkyl or $C_1$–$C_4$ hydroxyalkyl radical.

The oxidizing agent present in the dye composition is chosen from the oxidizing agents conventionally employed in oxidation dyeing and preferably from hydrogen peroxide, urea peroxide, alkali metal bromates and persalts such as perborates and persulphates. Hydrogen peroxide is particularly preferred.

The dye composition in accordance with the invention may also contain, in addition to the dyes defined above, other couplers and/or direct dyes, especially in order to modify the shades or to enrich them in highlights.

The suitable medium for the dyeing (or support) of the dye composition generally consists of water or of a mixture of water and of at least one organic solvent in order to solubilize the compounds which might not be sufficiently soluble in water. As an organic solvent it is possible to mention, for example, lower $C_1$–$C_4$ alkanols such as ethanol and isopropanol, glycerol, glycols and glycol ethers like 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents may be present in proportions which are preferably approximately between 1 and 40% by weight relative to the total weight of the dye composition, and still more preferably approximately between 5 and 30% by weight.

The dye compositions in accordance with the invention may also contain various adjuvants conventionally employed in the compositions for dyeing hair, such as anionic, cationic, nonionic, amphoteric or zwitterionic surface-active agents or mixtures thereof, anionic, cationic, nonionic, amphoteric or zwitterionic polymers or mixtures thereof, inorganic or organic thickening agents, antioxidants, penetrating agents, sequestering agents, perfumes, buffers, dispersing agents, conditioning agents, film-forming agents, preserving agents and opacifying agents.

The dye compositions in accordance with the invention may be presented in various forms, such as in the form of liquids, creams, gels or in any other suitable form for carrying out dyeing of keratinous fibres and especially of human hair.

A further subject of the invention is a process for dyeing keratinous fibres and in particular human keratinous fibres such as hair, making use of the dye composition as defined above.

According to this process the dye composition as defined above is applied to the fibres and is left in place approximately for 3 to 40 minutes, preferably approximately for 5 to 30 minutes, after which the fibres are rinsed, optionally washed with shampoo, rinsed again and dried.

According to a preferred embodiment the process comprises a preliminary stage consisting in storing in a separate form, on the one hand, a composition (A) including, in a suitable medium for dyeing, at least one oxidation base in accordance with the invention, 4-hydroxyindole and at least one additional benzene-based coupler in accordance with the invention and, on the other hand, a composition (B) containing, in a suitable medium for dyeing, at least one oxidizing agent as defined above, and in mixing them at the time of use before applying this mixture to the keratinous fibres, the pH of the compositions (A) and (B) being such that after mixing 10 to 90% of the composition (A) with 90 to 10% of the composition (B) the pH of the resulting mixture is higher than or equal to 7.

The pH of the compositions (A) and (B) may be adjusted to the desired value by means of alkalifying or acidifying agents which are conventional and such as defined above.

Another subject of the invention is a device with a number of compartments or dyeing kit or any other packaging system with a number of compartments in which a first compartment contains the composition (A) as defined above and a second compartment contains the oxidizing composition (B) as defined above. These devices may be equipped with a means, allowing the desired mixture to be delivered onto hair, such as the devices described in Patent FR-2 586 913 in the name of the Applicant Company.

The examples which follow are intended to illustrate the invention without, however, limiting its scope.

EXAMPLES

Examples 1 to 6

The following compositions 1(A) to 6(A), in accordance with the invention, were prepared (contents in grams):

| COMPOSITION | 1(A) | 2(A) | 3(A) | 4(A) | 5(A) | 6(A) |
|---|---|---|---|---|---|---|
| Para-aminophenol | 1 | | | | | |
| Para-phenylenediamine | | 0.3 | | | | |
| 3-Methyl-4-aminophenol | | | 0.3 | | | |
| 2,6-Dimethyl-para-phenylenediamine dihydrochloride | | | | 0.5 | | |
| 2-β-Hydroxyethyl-para-phenylenediamine dihydrochloride | | | | | 0.3 | |
| 3,4-Diaminopyrazole dihydrochloride | | | | | | 0.3 |
| 4-Hydroxyindole | 0.5 | 0.15 | 0.1 | 0.1 | 0.1 | 0.2 |
| 5-N-(β-Hydroxyethyl-amino)-2-methylphenol | 0.5 | | | | | 0.1 |
| 2-Methyl-5-aminophenol | | 0.2 | | | | |
| 2,4-Diamino-1-(β-hydroxyethoxy)- | | | 0.2 | | | |

-continued

| benzene hydrochloride | | | | | | | |
|---|---|---|---|---|---|---|---|
| 2-Amino-4-N-(β-hydroxy-ethylamino)anisole hydrochloride | | | | 0.4 | | | |
| Meta-aminophenol | | | | | | 0.2 | |
| Common dye base (*) | (*) | (*) | (*) | (*) | (*) | (*) | |
| Water q.s. | 100 g | 100 g | 100 g | 100 g | 100 g | 100 g | |

| (*) Common dye base: | |
|---|---|
| Oleyl alcohol polyglycerolated with 2 moles of glycerol | 4.0 g |
| Oleyl alcohol polyglycerolated with 4 moles of glycerol, containing 78% of active substances (A.S.) | 5.69 g A.S. |
| Oleic acid | 3.0 g |
| Oleylamine containing 2 moles of ethylene oxide, sold under the trade name Ethomeen O12 by Akzo | 7.0 g |
| Diethylaminopropyl laurylamino succinamate, sodium salt, containing 55% of A.S. | 3.0 g A.S. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulfite in aqueous solution containing 35% of A.S. | 0.455 g A.S. |
| Ammonium acetate | 0.8 g |
| Antioxidant, sequestrant | q.s. |
| Perfume, preservative | q.s. |
| Aqueous ammonia containing 20% of NH₃ | 10.0 g |

At the time of use each of these compositions 1(A) to 6(A) was mixed with an equal quantity of a composition (B) consisting of a 20-volume (6% by weight) aqueous hydrogen peroxide solution.

Each resulting composition (ready-for-use composition in accordance with the invention, of pH ≧7) was applied for 30 minutes to locks of grey hair containing 90% of white hair, natural or permanent-waved. The locks of hair were then rinsed, washed with a standard shampoo and then dried.

The locks of hair were dyed into the shades which appear in the table below:

| EXAMPLE [COMPOSITION] | SHADE ON NATURAL HAIR | SHADE ON PERMANENT-WAVED HAIR |
|---|---|---|
| 1[1(A)] | iridescent coppery blond | red iridescent coppery blond |
| 2[2(A)] | purple-violet blond | dark purple-violet blond |
| 3[3(A)] | light iridescent beige blond | iridescent blond |
| 4[4(A)] | ashen blue | deep blue |
| 5[5(A)] | slight ashen purple-violet | ashen purple-violet |
| 6[6(A)] | fuchsia pink | intense fuchsia pink |

Comparative Examples 7 and 8

The following examples 7(A) and 8(A) were prepared:

Composition 7(A) in accordance with the invention:

| Para-phenylenediamine | 0.4 g |
|---|---|
| 4-Hydroxyindole | 0.1 g |
| Meta-aminophenol | 0.3 g |
| Common dye base defined in Examples 1 to 6 | (*) g |
| Water q.s. | 100 g |

Composition 8(A) not forming part of the invention:

| Para-phenylenediamine | 0.4 g |
|---|---|
| 4-Hydroxyindole | 0.1 g |
| Resorcinol (additional coupler) | 0.3 g |
| Common dye base defined in Examples 1 to 6 | (*) g |
| Water q.s. | 100 g |

At the time of use each composition 7(A) and 8(A) was mixed with an equal quantity of a composition (B) consisting of a 20-volume (6% by weight) aqueous hydrogen peroxide solution.

Each resulting composition had a pH ≧7 and was applied for 30 minutes, on the one hand, to locks of natural grey hair containing 90% of white hair (lock No. 1 of unsensitized hair) and, on the other hand, to a lock of this same grey hair containing 90% of white but having been subjected to a permanent waving (lock No.2 of sensitized hair). The locks of hair were then rinsed, washed with a standard shampoo and then dried.

The colour of the locks was then evaluated in the Munsell system by means of a Minolta CM 2002 calorimeter.

According to the Munsell notation, a colour is defined by the expression HV/C in which the three parameters denote the shade or Hue (H), the intensity or Value (V) and the purity or Chromaticity (C) respectively; the oblique stroke in this expression is merely a convention and does not indicate a ratio.

The difference in colour between two locks is calculated by applying the Nickerson formula: $\Delta E = 0.4\ Co\Delta H + 6\Delta V + 3\Delta C$, as described, for example, in "Couleur, Industrie et Technique", pages 14–17, vol. No. 5, 1978.

In this formula, $\Delta E$ denotes the difference in colour between two locks, $\Delta H$, $\Delta V$ and $\Delta C$ denote the change in absolute value of the parameters H, V and C, and Co denotes the purity of the lock in relation to which it is desired to evaluate the difference in colour.

The results are given in the table below:

| EXAMPLE [COM-POSITION] | Colour on natural hair | Colour on permanent-waved hair | Difference in colour (selectivity) | | | |
|---|---|---|---|---|---|---|
| | | | ΔH | ΔV | ΔC | ΔE |
| 7[7(A)] | 3.6 R 2.5/1.0 | 9.4 RP 2.5/0.9 | 4.2 | 0 | 0.1 | 1.98 |
| 8[8(A)] | 6.5 YR 3.1/1.3 | 9.3 R 2.5/0.9 | 7.2 | 0.6 | 0.4 | 8.5 |

These results show that the composition of Example 7 in accordance with the invention produces a nonselective colour, which is not the case for the composition of Example 8, not forming part of the invention and containing a combination of para-phenylenediamine, 4-hydroxyindole and resorcinol as described, for example, in German Patent Application DE 3 031 709.

Comparative Examples 9 and 10

The following compositions 9(A) and 10(A) were prepared:

Composition 9(A) in accordance with the invention:

| 2,3-Dimethyl-para-phenylenediamine dihydrochloride | 0.4 g |
|---|---|
| 4-Hydroxyindole | 0.2 g |
| 2-Methyl-5-aminophenol | 0.2 g |

-continued

| | |
|---|---|
| Common dye base defined in Examples 1 to 6 | (*) g |
| Water q.s. | 100 g |

Composition 10(A) not forming part of the invention:

| | |
|---|---|
| 2,3-Dimethyl-para-phenylenediamine dihydrochloride | 0.4 g |
| 4-Hydroxyindole | 0.2 g |
| α-Naphthol (additional coupler) | 0.2 g |
| Common dye base defined in Examples 1 to 6 | (*) g |
| Water | 100 g |

At the time of use, each composition 9(A) and 10(A) was mixed with an equal quantity of a composition (B) consisting of a 20-volume (6% by weight) aqueous hydrogen peroxide solution.

Each resulting composition had a pH ≧7 and was applied for 30 minutes to locks of permanent-waved grey hair containing 90% of white hair. The locks of hair were then rinsed, washed with a standard shampoo and then dried.

The colour of the locks was then evaluated in the Munsell system by means of a Minolta CM 2002 calorimeter.

The locks of hair thus dyed were then subjected to a test for resistance to shampoos (Ahiba-Texomat machine):

The locks of hair were placed in a basket which was immersed in a solution of a standard shampoo at 37° C. The basket was subjected to a vertical forward and backward motion of variable frequency and to a rotational motion, reproducing the action of manual rubbing which gives rise to the formation of foam.

After 3 minutes of testing the locks were taken out and were rinsed and then dried. The dyed locks were subjected to 4 consecutive shampoo trials.

The colour of the locks was then again evaluated in the Munsell system by means of a Minolta CM 2002 calorimeter.

The shading-off of the colour due to the shampoos was calculated by applying the Nickerson formula as described above in Examples 7 and 8.

The results are given in the table below:

| EXAMPLE [COMPOSITION] | Hair colour before the shampoos | Hair colour after the shampoos | Shading-off of the colour | | | |
|---|---|---|---|---|---|---|
| | | | ΔH | ΔV | ΔC | ΔE |
| 9[9(A)] | 7.1 P 3.1/1.4 | 9.0 P 3.7/1.2 | 1.9 | 0.6 | 0.2 | 5.3 |
| 1[10(A)] | 1.1 RP 3.2/2.0 | 7.8 RP 3.9/1.5 | 6.7 | 0.7 | 0.5 | 11.1 |

These results show that the composition of Example 9 in accordance with the invention produces a colour which resists the shampoos much better than the composition of Example 10 not forming part of the invention and as described, for example, in German Patent Application DE 3 743 769.

What is claimed is:

1. A ready-for application composition for the oxidation dyeing of keratinous fibres comprising, in a suitable medium for dyeing:

at least one oxidation base of:

(i) a para-phenylenediamine of the following formula (I):

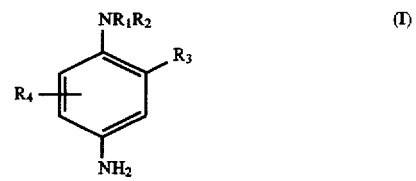

in which:

$R_1$ denotes a hydrogen atom or a $C_1$–$C_4$ alkyl, $C_1$–$C_4$ monohydroxyalkyl, $C_2$–$C_4$ polyhydroxyalkyl, $C_1$–$C_4$ alkoxyalkyl, phenyl or 4'-aminophenyl radical, $R_2$ denotes a hydrogen atom or a $C_1$–$C_4$ alkyl, $C_1$–$C_4$ monohydroxyalkyl or $C_2$–$C_4$ polyhydroxyalkyl radical, $R_3$ denotes a hydrogen atom, a halogen atom or a $C_1$–$C_4$ alkyl, $C_1$–$C_4$ monohydroxyalkyl or $C_1$–$C_4$ hydroxyalkoxy radical, $R_4$ denotes a hydrogen atom or a $C_1$–$C_4$ alkyl radical, provided that, when $R_4$ is other than hydrogen, then $R_1$ and $R_2$ denote a hydrogen atom and $R_3$ is identical with $R_4$, and the addition salts of these compounds of formula (I) with an acid;

(ii) the para-aminophenols of the following formula (II):

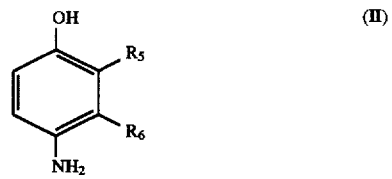

in which:

$R_5$ denotes a hydrogen atom or a $C_1$–$C_4$ alkyl, $C_1$–$C_4$ monohydroxyalkyl, $C_1$–$C_4$ alkoxyalkyl or $C_1$–$C_4$ aminoalkyl radical, $R_6$ denotes a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $C_1$–$C_4$ alkoxyalkyl radical, provided that at least one of the radicals $R_5$ and $R_6$ denotes a hydrogen atom, and the addition salts of these compounds of formula (II) with an acid;

(iii) heterocyclic bases of pyridine derivatives, pyrimidine derivatives, pyrazole derivatives and the addition salts of these heterocyclic bases with an acid; or (iv) ortho-aminophenol;

4-hydroxyindole as a first coupler;

at least one additional benzene-based coupler of the compounds of the following formula (III) and their addition salts with an acid:

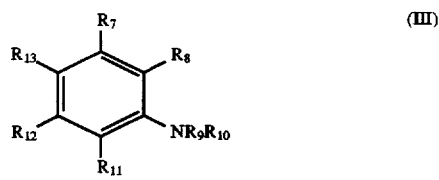

in which $R_7$ denotes an amino or hydroxyl radical, it being understood that:

when $R_7$ denotes an amino radical, then $R_8$ denotes a hydrogen atom or an alkyl radical, $R_9$ denotes a hydrogen atom, $R_{10}$ denotes a hydrogen atom or an alkyl, mono- or polyhydroxyalkyl radical, $R_{11}$ and $R_{12}$, which are identical or different, denote a hydrogen atom or an alkyl, mono- or polyhydroxyalkoxy radical, and $R_{13}$ denotes an alkoxy, aminoalkoxy or mono- or polyhydroxyalkoxy radical or a 2,4-diaminophenoxyalkoxy radical, provided that, if $R_{11}$ denotes a mono- or polyhydroxyalkoxy radical, then $R_{13}$ necessarily denotes a mono- or polyhydroxyalkoxy radical, when $R_7$ denotes a hydroxyl radical, then $R_8$ denotes a hydrogen atom, a halogen atom or an alkyl radical, $R_9$ denotes a hydrogen atom or an alkyl, mono- or polyhydroxyalkyl radical, $R_{10}$ denotes a hydrogen atom or an alkyl radical or forms with $R_9$ and the nitrogen atom a 5- or 6-cornered heterocyclic ring, $R_{11}$ denotes a hydrogen atom or an alkyl or alkoxy radical or a halogen atom, $R_{12}$ denotes a hydrogen atom and $R_{13}$ denotes a hydrogen atom or an alkyl, alkoxy, mono- or polyhydroxyalkyl, mono- or polyhydroxyalkoxy radical, provided that, if $R_8$ and $R_9$ simultaneously denote a hydrogen atom and $R_{13}$ a $C_1$–$C_4$ alkyl radical, then $R_{11}$ is other than a halogen atom or than a $C_1$–$C_4$ alkoxy radical, said alkyl, alkoxy, monohydroxyalkyl and monohydroxyalkoxy radicals contain from 1 to 4 carbon atoms, said polyhydroxyalkyl and polyhydroxyalkoxy radicals contain from 2 to 4 carbon atoms and from 2 to 3 hydroxyl groups, the halogen atom denoting chlorine, fluorine or bromine, at least one oxidizing agent, the pH of said ready-for application dye composition being greater than or equal to 7, wherein the at least one oxidation base, 4-hydroxyindole, at least one additional benzene-based coupler, and at least one oxidizing agent are present in an amount effective to oxidatively dye the keratinous fibers.

2. A composition according to claim 1, wherein the keratinous fibre is human hair.

3. A composition according to claim 1, wherein the addition salts with an acid are hydrochlorides, hydrobromides, sulphates and tartrates.

4. A composition according to claim 1, wherein the para-phenylenediamines of formula (I) are para-phenylenediamine, para-tolylenediamine, 2-isopropyl-para-phenylenediamine, 2-β-hydroxyethyl-para-phenylenediamine, 2-β-hydroxyethoxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 1-β-methoxyethylamino-4-aminobenzene or their addition salts with an acid.

5. A composition according to claim 1, wherein the para-phenylenediamines of formula (I) above are para-phenylenediamine, para-tolylenediamine, 2-β-hydroxyethyl-para-phenylenediamine, 2,6-dimethyl-para-phenylenediamine, 2,3-dimethyl-para-phenylenediamine and N,N-bis(β-hydroxyethyl)-para-phenylenediamine or their addition salts with an acid.

6. A composition according to claim 1, wherein the para-aminophenols of formula (II) are para-aminophenol, 3-methyl-4-aminophenol, 3-fluoro-4-aminophenol, 3-hydroxymethyl-4-aminophenol, 2-methyl-4-aminophenol, 2-hydroxymethyl-4-aminophenol, 2-methoxymethyl-4-aminophenol, 2-aminomethyl-4-aminophenol, 2-(β-hydroxyethyl-aminomethyl)-4-aminophenol or their addition salts with an acid.

7. A composition according to claim 1, wherein the para-aminophenols of formula (II) are para-aminophenol, 3-methyl-4-aminophenol, 3-fluoro-4-aminophenol and 3-hydroxymethyl-4-aminophenol or their addition salts with an acid.

8. A composition according to claim 1, wherein the heterocyclic bases are 2,4,5,6-tetraaminopyrimidine, 2,5-diaminopyridine, 4,5-diamino-1-methylpyrazole, 3,4-diaminopyrazole, 4-hydroxy-2,5,6-triaminopyrimidine or their addition salts with an acid.

9. A composition according to claim 1, wherein the additional benzene-based couplers (III) are meta-aminophenol, 2-methyl-5-aminophenol, 5-N-(β-hydroxyethylamino)-2-methylphenol, 5-amino-2-methoxyphenol, 5-amino-2-(β-hydroxyethoxy)phenol, 5-N-(β)-hydroxy-ethylamino)-4-methoxy-2-methylphenol, 5-amino-4-methoxy-2-methylphenol, 5-amino-4-chloro-2-methylphenol, 5-amino-2,4-dimethoxyphenol, 5-N-(γ-hydroxypropylamino)-2-methylphenol, 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diamino-phenoxy)methane, 2,4-diamino-1-(β-hydroxyethoxy)benzene, 1-(β-aminoethoxy)-2,4-diaminobenzene, 2-amino-1-β-hydroxyethoxy)-4-methylaminobenzene, 1,3-diamino-4,6-bis(β-hydroxyethoxy)benzene, 2,4-diamino-1-ethoxy-5-methylbenzene, 2,4-diamino-5-(β-hydroxyethoxy)-1-methylbenzene, 2,4-diamino-1-(β-hydroxyethoxy)-1-methylbenzene, 2,4-diamino-1-(β,γ-dihydroxypropoxy)benzene, 2-amino-4-N-(β-hydroxyethylamino)anisole or their addition salts with an acid.

10. A composition according to claim 1, wherein the additional benzene-based couplers are the compounds of formula (III) in which $R_9$ and $R_{10}$ denote a hydrogen atom.

11. A composition according to claim 10, wherein the additional benzene-based couplers are meta-aminophenol, 2-methyl-5-aminophenol, 5-N-(β-hydroxyethylamino)-2-methylphenol, 2,4-diamino-1-(β-hydroxyethoxy)benzene, 1,3-bis(2,4-diaminophenoxy)propane, 1,3-diamino-4,6-bis(β-hydroxyethoxy)benzene and 2-amino-4-N-(β-hydroxyethylamino)anisole or their addition salts with an acid.

12. A composition according to claim 1, wherein the amount of the oxidation base ranges from about 0.0005 to 10% by weight of the total weight of the dye composition.

13. A composition according to claim 12, wherein the amount of the oxidation base ranges from about 0.01 to 5% by weight of the total weight of the dye composition.

14. A composition according to claim 1, wherein the amount of the 4-hydroxyindole coupler ranges from about 0.0001 to 3.5% by weight of the total weight of the dye composition.

15. A composition according to claim 14, wherein the amount of the 4-hydroxyindole coupler ranges from about 0.005 to 1% by weight of the total weight of the dye composition.

16. A composition according to claim 1, wherein the amount of the compound of formula (III) ranges from about 0.0001 to 5% by weight of the total weight of the dye composition.

17. A composition according to claim 16, wherein the amount of the compound of formula (III) ranges from about 0.001 to 3% by weight of the total weight of the dye composition.

18. A composition according to claim 1, wherein the composition has a pH ranging from about 7 to 12.

19. A composition according to claim 18, wherein the composition has a pH ranging from about 8 to 11.

20. A composition according to claim 1, wherein the oxidizing agent is hydrogen peroxide, urea peroxide, alkali metal bromate, or persalt.

21. A composition according to claim 20, wherein the persalt is perborate or persulphate.

22. A composition according to claim 1, wherein the composition further comprises at least one adjuvant selected from anionic, cationic, nonionic, amphoteric and zwitterionic surface-active agents or mixtures thereof, anionic, cationic, nonionic, amphoteric and zwitterionic polymers or mixtures thereof, inorganic or organic thickening agents, antioxidants, penetrating agents, sequestering agents, perfumes, buffers, dispersing agents, conditioning agents, film-forming agents, preserving agents and opacifying agents.

23. A composition according to claim 1, wherein the composition is in the form of a liquid, a cream, a gel or any other suitable form for carrying out dyeing of keratinous fibres.

24. A process for dyeing keratinous fibres comprising the step of applying to the fibres at least one dye composition as claimed in claim 1.

25. A process for dyeing keratinous fibres comprising the steps of:

separately storing a composition (A) from a composition (B), wherein composition (A) comprises, in a suitable medium for dyeing, at least one oxidation base of:

(i) a para-phenylenediamine of the following formula (I):

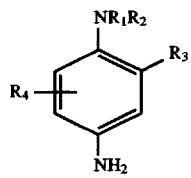

in which:

$R_1$ denotes a hydrogen atom or a $C_1$–$C_4$ alkyl, $C_1$–$C_4$ monohydroxyalkyl, $C_2$–$C_4$ polyhydroxyalkyl, $C_1$–$C_4$ alkoxyalkyl, phenyl or 4'-aminophenyl radical, $R_2$ denotes a hydrogen atom or a $C_1$–$C_4$ alkyl, $C_1$–$C_4$ monohydroxyalkyl or $C_2$–$C_4$ polyhydroxyalkyl radical, $R_3$ denotes a hydrogen atom, a halogen atom or a $C_1$–$C_4$ alkyl, $C_1$–$C_4$ monohydroxyalkyl or $C_1$–$C_4$ hydroxyalkoxy radical, $R_4$ denotes a hydrogen atom or a $C_1$–$C_4$ alkyl radical, provided that, when $R_4$ is other than hydrogen, then $R_1$ and $R_2$ denote a hydrogen atom and $R_3$ is identical with $R_4$, and the addition salts of these compounds of formula (I) with an acid;

(ii) the para-aminophenols of the following formula (II):

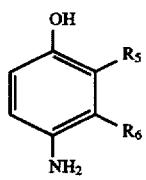

in which:

$R_5$ denotes a hydrogen atom or a $C_1$–$C_4$ alkyl, $C_1$–$C_4$ monohydroxyalkyl, $C_1$–$C_4$ alkoxyalkyl or $C_1$–$C_4$ aminoalkyl radical, $R_6$ denotes a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $C_1$–$C_4$ alkoxyalkyl radical, provided that at least one of the radicals $R_5$ and $R_6$ denotes a hydrogen atom, and the addition salts of these compounds of formula (II) with an acid;

(iii) heterocyclic bases of pyridine derivatives, pyrimidine derivatives, pyrazole derivatives and the addition salts of these heterocyclic bases with an acid; or (iv) ortho-aminophenol;

4-hydroxyindole as a first coupler; and at least one additional benzene-based coupler of the compounds of the following formula (III) and their addition salts with an acid:

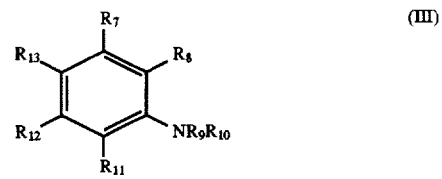

in which $R_7$ denotes an amino or hydroxyl radical, it being understood that:

when $R_7$ denotes an amino radical, then $R_8$ denotes a hydrogen atom or an alkyl radical, $R_9$ denotes a hydrogen atom, $R_{10}$ denotes a hydrogen atom or an alkyl, mono- or polyhydroxyalkyl radical, $R_{11}$ and $R_{12}$, which are identical or different, denote a hydrogen atom or an alkyl, mono- or polyhydroxyalkoxy radical, and $R_{13}$ denotes an alkoxy, aminoalkoxy or mono- or polyhydroxyalkoxy radical or a 2,4-diaminophenoxyalkoxy radical, provided that, if $R_{11}$ denotes a mono- or polyhydroxyalkoxy radical, then $R_{13}$ necessarily denotes a mono- or polyhydroxyalkoxy radical, when $R_7$ denotes a hydroxyl radical, then $R_8$ denotes a hydrogen atom, a halogen atom or an alkyl radical, $R_9$ denotes a hydrogen atom or an alkyl, mono- or polyhydroxyalkyl radical, $R_{10}$ denotes a hydrogen atom or an alkyl radical or forms with $R_9$ and the nitrogen atom a 5- or 6-cornered heterocyclic ring, $R_{11}$ denotes a hydrogen atom or an alkyl or alkoxy radical or a halogen atom, $R_{12}$ denotes a hydrogen atom and $R_{13}$ denotes a hydrogen atom or an alkyl, alkoxy, mono- or polyhydroxyalkyl, mono- or polyhydroxyalkoxy radical, provided that, if $R_8$ and $R_9$ simultaneously denote a hydrogen atom and $R_{13}$ a $C_1$–$C_4$ alkyl radical, then $R_{11}$ is other than a halogen atom or than a $C_1$–$C_4$ alkoxy radical, said alkyl, alkoxy, monohydroxyalkyl and monohydroxyalkoxy radicals contain from 1 to 4 carbon atoms, said polyhydroxyalkyl and polyhydroxyalkoxy radicals contain from 2 to 4 carbon atoms and from 2 to 3 hydroxyl groups, the halogen atom denoting chlorine, fluorine or bromine, and composition (B) comprises, in a suitable medium for dyeing, at least one oxidizing agent, and mixing said compositions (A) and (B) before applying this mixture to the keratinous fibres, applying the mixture to the keratinous fibres, the pH of the compositions (A) and (B) being such that, after mixing of 10 to 90% of the composition (A) with 90 to 10% of the composition (B) the pH of the resulting mixture is greater than or equal to 7, wherein the at least one oxidation base, 4-hydroxyindole, at least one additional benzene-based coupler, and at least one oxidizing agent are present in an amount effective to dye the keratinous fibers.

26. A process according to claim 25, wherein the oxidizing agent is hydrogen peroxide, urea peroxide, alkali metal bromate, or persalt.

27. A multicompartmented dyeing kit, comprising a first compartment that contains a composition (A), and a second compartment that contains an oxidizing composition (B) wherein composition (A) comprises, in a suitable medium for dyeing.

at least one oxidation base of:
(i) a para-phenylenediamine of the following formula (I):

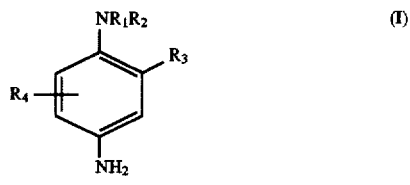

in which:

$R_1$ denotes a hydrogen atom or a $C_1$–$C_4$ alkyl, $C_1$–$C_4$ monohydroxyalkyl, $C_2$–$C_4$ polyhydroxyalkyl, $C_1$–$C_4$ alkoxyalkyl, phenyl or 4'-aminophenyl radical, $R_2$ denotes a hydrogen atom or a $C_1$–$C_4$ alkyl, $C_1$–$C_4$ monohydroxyalkyl or $C_2$–$C_4$ polyhydroxyalkyl radical, $R_3$ denotes a hydrogen atom, a halogen atom or a $C_1$–$C_4$ alkyl, $C_1$–$C_4$ monohydroxyalkyl or $C_1$–$C_4$ hydroxyalkoxy radical, $R_4$ denotes a hydrogen atom or a $C_1$–$C_4$ alkyl radical, provided that, when $R_4$ is other than hydrogen, then $R_1$ and $R_2$ denote a hydrogen atom and $R_3$ is identical with $R_4$, and the addition salts of these compounds of formula (I) with an acid,
(ii) the para-aminophenols of the following formula (II):

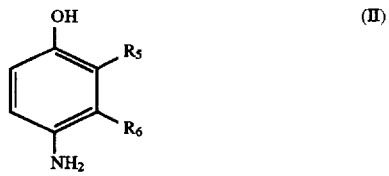

in which:

$R_5$ denotes a hydrogen atom or a $C_1$–$C_4$ alkyl, $C_1$–$C_4$ monohydroxyalkyl, $C_1$–$C_4$ alkoxyalkyl or $C_1$–$C_1$ aminoalkyl radical, $R_6$ denotes a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $C_1$–$C_4$ alkoxyalkyl radical, provided that at least one of the radicals $R_5$ and $R_6$ denotes a hydrogen atom, and the addition salts of these compounds of formula (II) with an acid;
(iii) heterocyclic bases of pyridine derivatives, pyrimidine derivatives, pyrazole derivatives and the addition salts of these heterocyclic bases with an acid; or
(iv) ortho-aminophenol;

4-hydroxyindole as a first coupler; and at least one additional benzene-based coupler of the compounds of the following formula (III) and their addition salts with an acid:

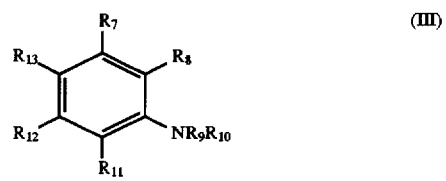

in which $R_7$ denotes an amino or hydroxyl radical, it being understood that:

when $R_7$ denotes an amino radical, then $R_8$ denotes a hydrogen atom or an alkyl radical, $R_9$ denotes a hydrogen atom, $R_{10}$ denotes a hydrogen atom or an alkyl, mono- or polyhydroxyalkyl radical, $R_{11}$ and $R_{12}$, which are identical or different, denote a hydrogen atom or an alkyl, mono- or polyhydroxyalkoxy radical, and $R_{13}$ denotes an alkoxy, aminoalkoxy or mono- or polyhydroxyalkoxy radical or a 2,4-diaminophenoxyalkoxy radical, provided that, if $R_{11}$ denotes a mono- or polyhydroxyalkoxy radical, then $R_{13}$ necessarily denotes a mono- or polyhydroxyalkoxy radical, when $R_7$ denotes a hydroxyl radical, then $R_8$ denotes a hydrogen atom, a halogen atom or an alkyl radical, $R_9$ denotes a hydrogen atom or an alkyl, mono- or polyhydroxyalkyl radical, $R_{10}$ denotes a hydrogen atom or an alkyl radical or forms with $R_9$ and the nitrogen atom a 5- or 6-cornered heterocyclic ring, $R_{11}$ denotes a hydrogen atom or an alkyl or alkoxy radical or a halogen atom, $R_{12}$ denotes a hydrogen atom and $R_{13}$ denotes a hydrogen atom or an alkyl, alkoxy, mono- or polyhydroxyalkyl, mono- or polyhydroxyalkoxy radical, provided that, if $R_8$ and $R_9$ simultaneously denote a hydrogen atom and $R_{13}$ a $C_1$–$C_4$ alkyl radical, then $R_{11}$ is other than a halogen atom or than a $C_1$–$C_4$ alkoxy radical, said alkyl, alkoxy, monohydroxyalkyl and monohydroxyalkoxy radicals contain from 1 to 4 carbon atoms, said polyhydroxyalkyl and polyhydroxyalkoxy radicals contain from 2 to 4 carbon atoms and from 2 to 3 hydroxyl groups, the halogen atom denoting chlorine, fluorine or bromine, and composition (B) comprises, in a suitable medium for dyeing, at least one oxidizing agent, and wherein the at least one oxidation base, 4-hydroxyindole, at least one additional benzene-based coupler, and at least one oxidizing agent are present in an amount effective to dye the keratinous fibers, the pH of the compositions (A) and (B) being such that, after mixing 10 to 90% of the composition (A) with 90 to 10% of the composition (B) the pH of the resulting mixture is greater than or equal to 7.

* * * * *

UNITED STATES PATENT AND TRADEMARK OFFICE
CERTIFICATE OF CORRECTION

PATENT NO. : 5,752,983
DATED : May 19, 1998
INVENTOR(S) : Marie-Pascale AUDOUSSET et al.

It is certified that error appears in the above-identified patent and that said Letters Patent is hereby corrected as shown below:

Claim 27, column 15, line 13, "$C_{2-4}$" should read --$C_2$-$C_4$--.

Signed and Sealed this

Fourteenth Day of July, 1998

Attest:

BRUCE LEHMAN

Attesting Officer    Commissioner of Patents and Trademarks